United States Patent [19]

Oduro-Yeboah

[11] Patent Number: 4,524,075
[45] Date of Patent: Jun. 18, 1985

[54] PHARMACEUTICAL FORMULATIONS CONTAINING PSEUDOMONIC ACID

[75] Inventor: Joshua Oduro-Yeboah, Worthing, England

[73] Assignee: Beecham Group p.l.c., England

[21] Appl. No.: 498,276

[22] Filed: May 26, 1983

[30] Foreign Application Priority Data

May 28, 1982 [GB] United Kingdom ............... 8215684
May 12, 1983 [GB] United Kingdom ............... 8313036

[51] Int. Cl.³ .............................................. A61K 31/44
[52] U.S. Cl. .................................... 514/451; 514/723
[58] Field of Search ................................ 424/180, 283

[56] References Cited

U.S. PATENT DOCUMENTS

| | | | |
|---|---|---|---|
| 4,256,762 | 3/1981 | Luk et al. | 424/283 |
| 4,283,411 | 8/1981 | Luk et al. | 424/283 |
| 4,283,412 | 8/1981 | Luk et al. | 424/283 |
| 4,289,779 | 9/1981 | Luk et al. | 424/283 |
| 4,312,874 | 1/1982 | Rogers et al. | 424/283 |

OTHER PUBLICATIONS

Wuite et al., "Chem. Abst.", vol. 99, 1983, P172689(s).

Primary Examiner—Johnnie R. Brown
Attorney, Agent, or Firm—Jacobs & Jacobs

[57] ABSTRACT

Topical formulations comprise pseudomonic acid or a salt or ester thereof and a polyethylene glycol or polyethylene glycol analogue or derivative.

20 Claims, No Drawings

PHARMACEUTICAL FORMULATIONS CONTAINING PSEUDOMONIC ACID

The present invention relates to pharmaceutical formulations, for topical use, which contain pseudomonic acid or a salt or ester thereof as sole therapeutic agent.

Pseudomonic acid, its salts and esters, are known antibiotic agents and are described in U.K. Pat. No. 1,395,907. These agents are useful in treating skin, ear and eye disorders by topical administration. Various topical formulations of pseudomonic acid have been produced but have not been sufficiently stable for commercial exploitation. It has now been surprisingly found that, in the presence of polyethylene glycol, or a derivative thereof, pseudomonic acid has improved stability.

Accordingly, the present invention provides a topical formulation comprising pseudomonic acid, or a salt or ester thereof and at least 1% by weight of a poly(substituted or unsubstituted alkylene)glycol or a derivative thereof.

As used herein the term 'poly(substituted or unsubstituted alkylene)glycol' refers to polymers having the following repeating unit $$-(CH_2)_nO-$$

wherein n is an integer, preferably 2 or 3 and to such polymers wherein one or more methylene groups of each repeating unit is substituted. Suitable substituents include alkoxy groups such as methoxy as in polymethoxypropylene glycol. Such polymers are known by a variety of names, for instance when n=2, as polyethylene glycol, polyoxyethylene, polyoxyethylene glycol and macrogol and, when n=3, as polypropylene glycol, polyoxypropylene and polyoxypropylene glycol. All these are useful in the invention as are derivatives of these polymers.

Suitable derivatives include ethers and esters of the poly(substituted or unsubstituted alkylene) glycols, such as the macrogol ethers and esters, for instance cetomacrogol, glycofurol, the 'Tweens'* and block copolymers including poly(substituted or unsubstituted alkylene)glycols such as Poloxamers which are block copolymers of polyethylene glycol and polypropylene glycol for instance the 'Pluronics'*, and cross-linked polyethylene glycol.

*'Tween' and 'Pluronic' are trade names for the above types of polymer.

The poly(substituted or unsubstituted alkylene) glycols and derivatives thereof may be used singly or various grades and types may be used in combination to achieve the desired physical properties of the formulation.

Preferably the formulation comprises polyethylene glycol or a derivative thereof.

Suitably the formulation comprises from 0.01 to 50% by weight of pseudomonic acid or a salt or ester thereof, preferably 0.1 to 25%, more preferably 0.5 to 10% and most preferably about 2% by weight of pseudomonic acid or a salt or ester thereof. Such formulations comprising only pseudomonic acid or a salt or ester thereof and a poly(substituted or unsubstituted alkylene)glycol or derivative thereof will, of course, contain up to 99.99% of the poly (substituted or unsubstituted alkylene)glycol or derivative thereof.

The formulation may comprise additional therapeutic agents such as antibacterial, antifungal, antiviral and antiinflammatory agents, for instance chlortetracycline, miconazole, idoxuridine and phenazone, provided that these are compatible with the pseudomonic acid or salt or ester thereof. Pseudomonic acid and its salts and esters tend to undergo a rearrangement reaction in the presence of acid and accordingly acidic agents are unlikely to be compatible with pseudomonic acid and its salts and esters.

In a particular aspect the invention provides a formulation as described above wherein pseudomonic acid, or a salt or ester thereof, is the sole thereapeutic agent.

In another aspect the invention provides a topical formulation comprising pseudomonic acid or a salt or ester thereof and at least 1% by weight of polyethylene glycol or a derivative thereof.

Polyethylene glycols (PEG's) and derivatives thereof are commercially available in a variety of chain lengths and with a variety of consistencies, for instance:

Polyethylene Glycols:

| Liquids | Semisolids | Hard Solids |
| --- | --- | --- |
| PEG 200 | PEG 1000 | PEG 4000* |
| PEG 300 | PEG 1540 | PEG 6000 |
| PEG 400 | | |

*PEG 4000 is the B.P. nomenclature for PEG with mean molecular weight of 3350. This material is also known as PEG 3350 in U.S.P. nomenclature.

Polyethylene Glycol derivatives:

| Derivative | Chemical Composition | Consistency |
| --- | --- | --- |
| Glycofurol | Tetrahydrofurfuryl alcohol polyethylene glycol ether | Liquid |
| Tween 60 | Polyoxyethylene Sorbitan monostearate | Semi-solid |
| Tween 80 | Polyoxyethylene Sorbitan monooleate | Liquid |

These may be used singly or admixed in suitable proportions to achieve the desired consistency of formulation.

The formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams. The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Suitable salts of pseudomonic acid include alkali metal salts, especially sodium pseudomonate.

Suitable esters of pseudomonic acid include lower alkyl esters, especially methyl or ethyl pseudomonate.

Preferably the therapeutic agent is pseudomonic acid.

Particularly suitable formulations according to the present invention comprise at least 1% by weight of PEG or a mixture of PEG's, from 0 to 25% by weight of a PEG derivative or mixture of PEG derivatives and from 0.5 to 10% by weight of pseudomonic acid or a salt or ester thereof.

Preferably the pseudomonic acid or salt or ester thereof represents 1 to 5% of the formulation, most preferably about 2% of the formulation.

Formulations of the invention may be produced by conventional pharmaceutical techniques. Thus ointments and creams are conveniently prepared by melting and mixing together the solid or semi-solid PEG's or PEG analogues or derivatives, and stirring in the therapeutic agent and any other ingredients. The product is then slowly cooled and filled into containers such as collapsible metal or plastic tubes.

Liquid preparations, such as ear and eye drops, are produced by dissolving the therapeutic agent in the liquid PEG's or PEG analogues or derivatives and the other ingredients are then added. The resulting solution or suspension is distributed into glass or plastic bottles or in single dose packs such as soft gelatin capsules which are then heat sealed.

If necessary the formulation may be milled at any suitable stage of the process.

A suitable sterilisation procedure may be included in the above processes if necessary. Alternatively raw materials are obtained in sterile conditions and the formulations are produced aseptically.

The invention will now be illustrated by the following Examples:

EXAMPLE 1

Liquid Formulation

Pseudomonic acid is dissolved in PEG 400 and the formulation adjusted, by addition of further PEG 400, to contain 2% by weight of pseudomonic acid.

EXAMPLE 2

Ointment Formulation

|  | % w/w |
|---|---|
| PEG 400 | 59 |
| PEG 4000 | 39 |
| Pseudomonic Acid | 2 |

The formulation is produced by melting the mixture of PEG's and stirring in the pseudomonic acid.

EXAMPLE 3

Lotion Formulation

|  | % w/w |
|---|---|
| PEG 400 | 74 |
| Ethanol | 24 |
| Pseudomonic acid | 2 |

EXAMPLE 4

Drop Formulation

|  | % w/w |
|---|---|
| PEG 400 | 74 |
| Glycofurol | 24 |
| Pseudomonic acid | 2 |

EXAMPLE 5

|  | % w/w |
|---|---|
| Cetomacrogol emulsifying ointment | 65 |
| Polyethylene glycol 200 | 33 |
| Pseudomonic acid | 2 |

Stability Test

The stability of the formulations in Examples 1 and 2 was compared with that of pseudomonic acid alone by storing samples at either 30° or 37° C. for 12 months. The amount of therapeutic agent remaining at 2 months and at the end of this period was assayed and is given in the Table:

| | % remaining after | | | |
|---|---|---|---|---|
| | 2 months | | 12 months | |
| Formulation | 30° C. | 37° C. | 30° C. | 37° C. |
| Pseudomonic acid | 78 | Dec* | Dec | Dec |
| Example 1 | 98 | 97 | 91 | 87 |
| Example 2 | 100 | 90 | 92 | 89 |

*Dec - melted with decomposition.

I claim:

1. A highly stable pharmaceutical composition in topical application form which comprises an antibacterially effective amount of pseudomonic acid, a pharmaceutically acceptable salt thereof or a pharmaceutically acceptable ester thereof and a stabilizing amount of at least 1% by weight of a poly(alkylene)glycol, a poly(alkoxy substituted alkylene)glycol, a pharmaceutically acceptable ether thereof, a pharmaceutically acceptable ester thereof or a mixture thereof.

2. A formulation according to claim 1 comprising from 0.01 to 50% by weight of pseudomonic acid or a salt or ester thereof.

3. A formulation according to claim 2 comprising from 0.1 to 25% by weight of pseudomonic acid or a salt or ester thereof.

4. A formulation according to claim 3 comprising from 0.5 to 10% by weight of pseudomonic acid or a salt or ester thereof.

5. A formulation according to claim 4 comprising about 2% by weight of pseudomonic acid or a salt or ester thereof.

6. A formulation according to claim 1 wherein pseudomonic acid or a salt or ester thereof is the sole therapeutic agent.

7. A formulation according to claim 1 wherein the pseudomonic acid, salt or ester is in the form of the acid.

8. A formulation according to claim 1 wherein the pseudomonic acid, salt or ester is in the form of an alkali metal salt.

9. A formulation according to claim 8 in the form of an alkali metal salt wherein the alkali metal salt is sodium pseudomonate.

10. A formulation according to claim 1 wherein the pseudomonic acid, salt or ester is in the form of an alkyl ester of 1 to 4 carbon atoms.

11. A formulation according to claim 10 wherein the alkyl ester is methyl or ethyl pseudomonate.

12. A formulation according to claim 1 wherein the glycol is polyethylene glycol.

13. A formulation according to claim 1 which contains at least 1% by weight of polyethylene glycol or a mixture of polyethylene glycols and from 0 to 25% by weight of a poly(alkoxy substituted alkylene)glycol, a pharmaceutically acceptable ether thereof, a pharmaceutically acceptable ester thereof or a mixture thereof.

14. A formulation according to claim 13 which contains polyethylene glycol 400 and polyethylene glycol 4000.

15. A formulation according to claim 13 which contains polyethylene glycol 400 and glycofurol or cetomacrogol.

16. A formulation according to claim 13 which contains from 0.5 to 10% of pseudomonic acid or a salt or ester thereof.

17. A formulation according to claim 14 which contains from 0.5 to 10% of pseudomonic acid or a salt or ester thereof.

18. A formulation according to claim 15 which contains from 0.5 to 10% of pseudomonic acid or a salt thereof.

19. A formulation according to claim 1 in lotion, cream or ointment form.

20. A formulation according to claim 1 in the form of drops for application to the ears or eyes.

* * * * *